United States Patent [19]

Mauersberger et al.

[11] Patent Number: 4,651,960

[45] Date of Patent: Mar. 24, 1987

[54] MOTOR DRIVEN MOUNTING APPARATUS FOR AN IRRADIATION DEVICE SUCH AS A SUNLAMP OR THE LIKE

[75] Inventors: Winfrid Mauersberger, Ascheberg-Herbern; Karl H. Mauersberger, Dortmund, both of Fed. Rep. of Germany

[73] Assignee: Mainz & Mauersberger Alu-System GmbH, Dortmund, Fed. Rep. of Germany

[21] Appl. No.: 777,595

[22] Filed: Sep. 19, 1985

[30] Foreign Application Priority Data

May 18, 1985 [DE] Fed. Rep. of Germany ....... 3518009

[51] Int. Cl.⁴ ........................................... F16M 13/00
[52] U.S. Cl. .................. 248/292.1; 16/241; 16/289
[58] Field of Search ................ 248/123.1, 292.1, 364, 248/667, 666, 561; 16/289, 306, 357, 241, 245, 246, 305; 292/254

[56] References Cited

U.S. PATENT DOCUMENTS

| | | | |
|---|---|---|---|
| 2,179,357 | 11/1939 | Stava | 248/292.1 X |
| 3,039,804 | 6/1962 | Quinn | 292/254 |
| 3,838,877 | 10/1974 | Hanson | 292/254 |
| 4,277,044 | 7/1981 | Hamilton | 248/292.1 |
| 4,441,376 | 4/1984 | Tubey | 16/241 X |
| 4,528,897 | 7/1985 | Homolik | 16/289 X |

FOREIGN PATENT DOCUMENTS 2106172 4/1983 United Kingdom ................ 16/245

*Primary Examiner*—Robert W. Gibson, Jr.
*Assistant Examiner*—David L. Talbott
*Attorney, Agent, or Firm*—Toren, McGeady and Goldberg

[57] ABSTRACT

Mounting apparatus for an irradiation device, such as a sunlamp or the like, wherein a mounting bracket pivotally supported on a frame has an irradiation device operatively supported thereon and wherein a drive motor pivotally moves the mounting bracket relative to the frame. A connection mechanism interposed between the drive motor and the mounting bracket includes bearing recesses formed in the mounting bracket, a lifting nut having a pair of articulated pins engaging in the bearing recesses and a lifting spindle driven by the drive motor and having the lifting nut operatively mounted thereon. A mechanically actuated release lever engages the lifting spindle for moving the articulated pins out of engagement with the bearing recesses, and a spring interposed between the frame and the mounting bracket applies a spring biasing force pivotally urging the mounting bracket in a direction for lifting the mounting bracket when the articulated pins are moved out of engagement with the bearing recesses.

2 Claims, 3 Drawing Figures

MOTOR DRIVEN MOUNTING APPARATUS FOR AN IRRADIATION DEVICE SUCH AS A SUNLAMP OR THE LIKE

The present invention is directed toward apparatus for mounting a sunlamp or similar irradiation device, and, more particularly, to apparatus including a motor driven mechanism for lifting and lowering the irradiation element or sunlamp. More particularly, the invention is directed toward the type of device, wherein a pivotable support element or mounting bracket upon which the irradiation device is mounted is placed under a spring tension when it is lowered so that, during a failure or inoperativeness of the drive mechanism of the lifting device, the irradiation device may be lifted automatically to avoid injury or malfunction. Such a spring actuated fail-safe operation may occur, for example, when the driving mechanism is separated from the part upon which the irradiation device is mounted so as to automatically bring the device into a safe position. The drive mechanism or lifting device may be constructed as a lifting spindle which is actuated by means of a motor having a lifting nut which acts upon the support element for the sunlamp or irradiation device.

A device of this type is known in the art from DE-OS 33 10 213, wherein electrical or electronic means are provided in order to separate the lifting mechanism from the upper mounting element during outage of the drive mechanism of the lifting device by a spreading action, whereby a two-piece lifting nut is spread apart from the lifting spindle. In practice, however, this type of construction causes problems due to failure of the electronics and contact difficulties arise so that it is not always possible to insure a secure raising of the irradiation device in such a way that a person exposed to the radiation may leave the device without difficulty.

Accordingly, the present invention is directed toward providing a mechanism involving simple mechanical means which will safely insure lifting of the part upon which the irradiation device or sunlamp is mounted during failure of the drive mechanism of the lifting device.

SUMMARY OF THE INVENTION

Briefly, the present invention may be described as a mounting apparatus for an irradiation device, such as a sunlamp or the like, comprising frame means, a mounting bracket pivotally supported on said frame means adapted to have an irradiation device, such as a sunlamp or the like, operatively supported thereon, a drive motor for pivotally moving said mounting bracket relative to said frame means and connecting means interposed between the drive motor and the mounting bracket. The connecting means comprise bearing recesses formed in the mounting bracket, a lifting nut having a pair of articulated pins engaged in the bearing recesses and a lifting spindle driven by the drive motor and having the lifting nut operatively mounted thereon. A mechanically actuated release lever is provided for engaging the lifting spindle to move the articulated pins out of engagement with the bearing recesses and first spring means are interposed between the frame means and the mounting bracket applying a spring biasing force pivotally urging the mounting bracket in a first direction for lifting the mounting bracket when the articulated pins are moved out of engagement with the bearing recesses.

Thus, in accordance with the invention, the objectives thereof are met in that the lifting nut is supported with the articulated pins on both sides in the bearing recesses which are open at one side at a fastening part for the mounting bracket and, by means of the mechanically actuated drawing release lever acting against the lifting spindle, the lifting nut is movable out of engagement with the bearing recesses in such a way that the mounting bracket moves upwardly under the action of the first spring means.

It has been shown that an absolutely secure actuation is insured in such a construction with a relatively small expenditure of manual force, for example, with the utilization of a Bowden cable acting on the release lever, which is dimensioned so as to be appropriately long.

In addition, it is suggested in a particularly advantageous embodiment of the invention to provide the bearing recesses with stopping or locking recesses which are directly vertically relative to the release movement of the articulated pins of the lifting nut and into which the articulated pins may enter so as to become locked under the action of the first spring means insofar as the upper part is not yet mounted or assembled at the fastening part. It is insured, that is, by means of this construction that no such critical situations can occur during mounting assembly of the device as could occur during an unintentional actuation of the release lever if the fastening part is moved in the horizontal position, but the heavy irradiation upper part is not yet mounted, because then, the forces of approximately 5000 n stored in the spring effecting the upward movement of the upper part in cases of need, would be released in a jerky manner, wherein a fastening part could fly up and cause severe personal injuries.

In order to insure that the supporting device for enabling the lifting or upward movement of the upper part in case of need is operative in the completely mounted state of the device, a second spring is provided, and a further development of the invention, which acts on a pawl articulated at the fastening part when the upper part is mounted at the fastening part in the lowered position of the latter in such a way that the swivelable pawl moves the articulated pins of the lifting nut out of the stopping recesses in the releasing position in such a way that the separating process can then be effected at a lower expenditure of force during an actuation of the release lever.

In order to provide for an exactly correct position of the articulating pins, a stop may be provided to define the swiveling movement of the pawl, which is effected under the influence of the second spring in such a way that the articulated pins of the lifting nut are exactly located in the release position.

The various features of novelty which characterize the invention are pointed out with particularity in the claims annexed to and forming a part of this disclosure. For a better understanding of the invention, its operating advantages and specific objects attained by its use, reference should be had to the drawings and descriptive matter in which there is illustrated and described a preferred embodiment of the invention.

DETAILED DESCRIPTION OF THE PREFERRED EMBODIMENT

Figure 1:
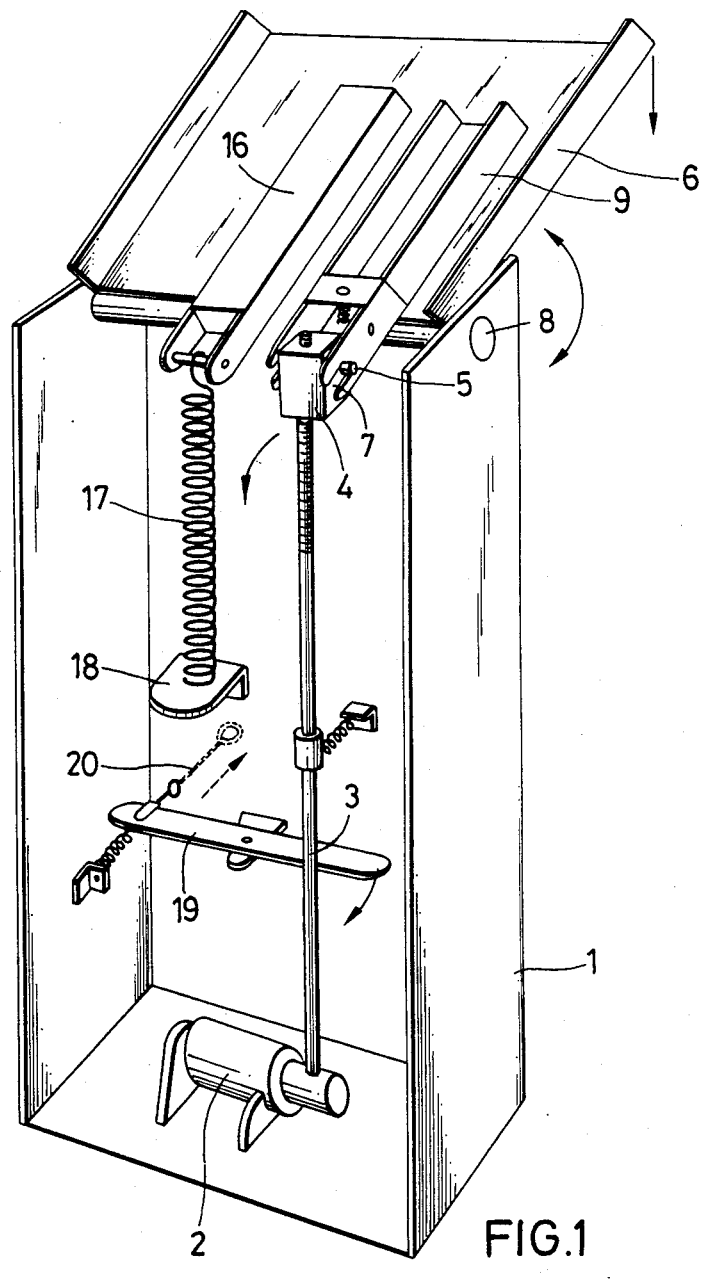
FIG. 1 is a perspective view showing a mounting apparatus in accordance with the present invention.

Referring now to the drawings, wherein there is depicted an embodiment of the present invention, the apparatus of the invention is shown as comprising a support frame 1 having an electrical drive motor 2 mounted therein. The drive motor 2 comprises a worm gear unit for actuating a lifting spindle 3 having a lifting nut 4 attached at the upper part thereof. The lifting nut 4 is provided with lateral articulated pins 5 which engage in bearing recesses 7 which are open at one side of a fastening part which is designated in its entirety by reference numeral 6 and which comprises an upper part or mounting bracket for the apparatus upon which an irradiation device (not shown), such as a sunlamp, may be operatively mounted.

Figure 3:
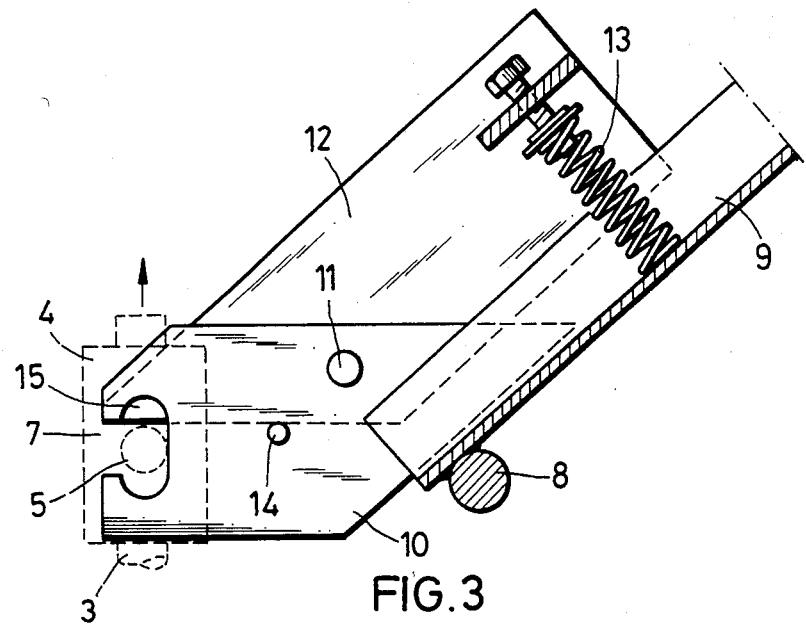
FIG. 3 is a sectional view taken along the line A—A of FIG. 2.
Figure 2:
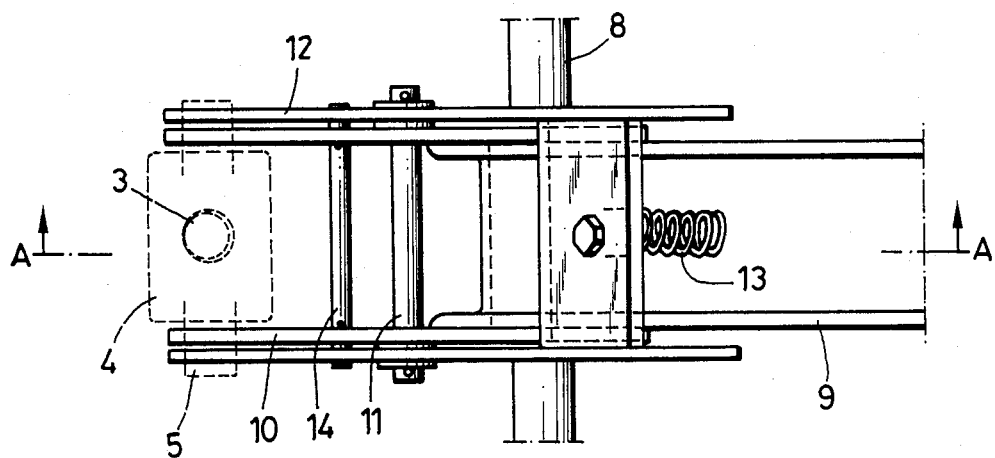
FIG. 2 is a top view of a part of the apparatus of FIG. 1.

The mounting bracket 6 is supported at the vertical support frame 1 so as to be capable of pivotal movement about a horizontal pivot axle 8. The bracket 6 comprises a U-shaped support arm 9 at its upper side which is rigidly fastened at the mounting bracket 6 and which includes supporting brackets 10 at both sides of its cantilevering end, with the bearing recesses 7 being located in the support brackets 10. A swivel axle 11 extends through the support brackets 10 and a forked pawl 12 is arranged so as to be pivotally mounted on the axle 11. The forked pawl 12 is under the influence of a second spring 13 which acts on the pawl 12 in the counterclockwise direction, as seen in FIG. 3.

Pivotal movement of the pawl 12 under the influence of the spring 13 is limited by means of a stop pin 14 which is likewise fastened between the supporting brackets 10. The bearing recesses 7 are provided with upper locking slots 15 into which the articulated pins 5 may enter so as to be placed into stopping or locking engagement.

An additional supporting arm 16 attached to the mounting bracket 6 is formed with a cantilevering end at which a first spring 17 is connected, the other end of the first spring 17 being attached at a spring bracket 18 which is affixed to the vertical support frame 1. Additionally, a twin-armed release lever 19 is mounted in pivoting or articulated engagement with the support frame 1 with one end of the release lever 19 being connected with a Bowden cable 20 and the other end of the lever 19 being arranged to act against the lifting spindle 3 during actuation of the Bowden cable 20 in such a way and in such a direction that the lifting nut 4 is moved so that the pins 5 will be taken out of engagement from within the bearing recesses 7. As a result of this, the mounting bracket 6 having the irradiation device (not shown) mounted thereon will be moved through a pivotal motion in one direction around the horizontal pivot axle 8 under the influence of the first spring 17.

In the operation of the device of the present invention, during mounting or assembly of the device, the mounting bracket 6 is first moved to a horizontal position. In this position, the force of the first spring 17 causes the articulated pins 5 at the lifting nut 4 to be securely pressed into the locking slots 15, wherein the effect of the second spring 13 acting upon the pawl 12, which spring 13 is dimensioned so as to be correspondingly weaker to overcome in such a way that the pawl 12 is lifted and the articulated pins 5 are stopped. Unintentional disengagement of the articulated pins 5 and, with this, a sudden upward movement of the mounting bracket 6 under the force of the strong first spring 17 is accordingly prevented, and the upper part of the irradiation device may be easily mounted at the mounting bracket 6.

As soon as this mounting is effected, and, accordingly, the weight of the heavy upper part substantially compensates the action of the first spring 17, the action or effect of the second spring 13 comes into action and presses the pawl 12 into the releasing position shown in FIG. 3, wherein the stop pin 14 provides for an exactly correct achievement of the releasing position.

Because the compensation of the occurring forces, due to the inherent weight of the upper part of the irradiation device, and because of the spring force of the first spring 17, only slight frictional forces occur in this state between the articulated pins 5 and the bearing recesses 7. The apparatus is therefore conditioned in case of a need to allow the articulated pins 5 to be released from the bearing recesses 7, as is indicated by means of the arrow shown extending from the lifting nut 4 in FIG. 1, by means of the actuation of the Bowden cable 2 accompanied by the application of only slight actuating forces. As soon as the articulated pins are free of the bearing recesses 7, the upper part (not shown) of the irradiation device can slowly swivel upwardly under the slight excess force of the first spring 17 so that a person located in the irradiation device can leave the device conveniently and without danger of harm.

Thus, in accordance with the foregoing, in an apparatus for the motor driven lifting and lowering of the upper part of an irradiation device, particularly of a sunlamp or the like, wherein, when the upper part is lowered, a first spring acting on the latter is tensioned, its spring force lifting the upper part when, during a failure of the drive energy of a lifting device, the latter is separated from the upper part, wherein the lifting device is constructed as a lifting spindle which is drivable by means of a motor and whose lifting nut acts on the upper part, a solution is provided which, with simple mechanical means, safely insures upward movement of the upper part during failure of the drive energy of the lifting device.

This is achieved in that the lifting nut 4 is supported with articulated pins 5 at the two sides in bearing recesses 7 open at one side at a fastening part 6 for the upper part and, by means of a mechanically actuated release lever 19 acting against the lifting spindle 3, is movable out of these bearing recesses 7 in such a way that the upper part moves upwardly under the influence of the first spring 17 likewise acting at the fastening part.

While a specific embodiment of the invention has been shown and described in detail to illustrate the application of the inventive principles, it will be understood that the invention may be embodied otherwise without departing from such principles.

What is claimed:

1. Mounting apparatus for an irradiation device, such as a sunlamp or the like, comprising:
    frame means;
    a mounting bracket pivotally supported on said frame means adapted to have an irradiation device, such as a sunlamp or the like, operatively supported thereon;

a drive motor for pivotally moving said mounting bracket relative to said frame means;

connection means interposed between said drive motor and said mounting bracket, said connection means comprising bearing recesses formed in said mounting bracket, a lifting nut having a pair of articulated pins engaging in said bearing recesses and a lifting spindle driven by said drive motor and having said lifting nut operatively mounted thereon;

a mechanically actuated release lever engaging said lifting spindle for moving said articulated pins out of engagement with said bearing recesses;

first spring means interposed between said frame means and said mounting bracket applying a spring biasing force pivotally urging said mounting bracket in a direction for lifting said mounting bracket when said articulated pins are moved out of engagement with said bearing recesses;

said bearing recesses being formed with locking slots directed vertically relative to the releasing movement of said articulated pins of said lifting nut, said articulated pins entering into said locking slots so as to stop under the influence of said first spring means insofar as said irradiation device is not mounted on said mounting bracket; and second spring means acting on a pawl articulated at said mounting bracket when said irradiation device is mounted at said mounting bracket, in the lowered position of said irradiation device in such a way that said pawl is swivelable and moves said articulated pins of said lifting nut out of said locking slots in the releasing position.

2. Apparatus according to claim 1, wherein a stop member is provided defining the limit of the swiveling movement of said pawl, which swiveling movement is effected under the influence of said spring means in such a manner that said articulated pins of said lifting nut are located exactly in said release position.

* * * * *